(12) United States Patent
Harrison

(10) Patent No.: US 9,903,850 B2
(45) Date of Patent: Feb. 27, 2018

(54) MEASUREMENT OF SUGAR IN A SOLUTION

(71) Applicant: Salunda Limited, Oxfordshire (GB)

(72) Inventor: Martin Roy Harrison, Northants (GB)

(73) Assignee: Salunda Limited, Oxfordshire (GB)

( * ) Notice: Subject to any disclaimer, the term of this patent is extended or adjusted under 35 U.S.C. 154(b) by 170 days.

(21) Appl. No.: 14/970,140

(22) Filed: Dec. 15, 2015

(65) Prior Publication Data

US 2016/0178601 A1 Jun. 23, 2016

(30) Foreign Application Priority Data

Dec. 19, 2014 (GB) ............................ GB1422797.9

(51) Int. Cl.
*G01N 33/28* (2006.01)
*G01N 22/00* (2006.01)
*G01N 27/02* (2006.01)

(52) U.S. Cl.
CPC ......... *G01N 33/2835* (2013.01); *G01N 22/00* (2013.01); *G01N 27/026* (2013.01)

(58) Field of Classification Search
CPC ...... G01N 27/00; G01N 27/02; G01N 27/026; G01N 22/00; G01N 33/00; G01N 33/26; G01N 33/28; G01N 33/2835; G01N 21/7746; G01N 2021/7789; G01N 2291/014; G01R 27/00; G01R 27/02;
(Continued)

(56) References Cited

U.S. PATENT DOCUMENTS

| 3,879,653 A | * 4/1975 | Hyde | ................... G01R 33/60 324/316 |
|---|---|---|---|
| 5,103,180 A | * 4/1992 | Lahitte | ................... G01N 22/00 324/629 |
| 5,483,172 A | 1/1996 | Radford | |

(Continued)

FOREIGN PATENT DOCUMENTS

| WO | WO-2003/012413 A2 | 2/2003 |
|---|---|---|
| WO | WO-2007109772 A2 | 9/2007 |

(Continued)

OTHER PUBLICATIONS

X. Bohigas et al., Food Research International Published 2008, vol. 41, pp. 104-109, "Characterisation of sugar content in yoghurt by means of microwave spectroscopy".

(Continued)

*Primary Examiner* — Hoai-An D Nguyen
(74) *Attorney, Agent, or Firm* — Honigman Miller Schwartz and Cohn LLP

(57) ABSTRACT

A system and method for measuring the amount of sugar in a sample including measuring a solution of the sugar using oscillating electromagnetic fields generated in the sample at least two radio frequencies at which the electromagnetic properties of the solution differ. There are detected characteristics of the oscillating electromagnetic fields generated in the sample at each radio frequency that are dependent on the electromagnetic properties of the solution. A measure of the amount of sugar is derived from those characteristics. By combining measurements at different radio frequencies, the effects of changes in the ion concentration can then be removed to give an unambiguous measure for the sugar.

23 Claims, 5 Drawing Sheets

(58) Field of Classification Search
CPC ........ G01R 27/04; G01R 27/06; G01R 27/26;
G01R 27/28; A61B 5/14532
USPC ....... 324/600, 629, 633, 636, 637, 639, 640,
324/649, 652; 600/300, 309, 310, 316,
600/318, 319, 345, 347, 365
See application file for complete search history.

(56) References Cited

U.S. PATENT DOCUMENTS

| | | | |
|---|---|---|---|
| 6,249,129 B1 | 6/2001 | Burk et al. | |
| 6,359,444 B1* | 3/2002 | Grimes | G01N 22/00 |
| | | | 324/633 |
| 7,135,869 B2* | 11/2006 | Sergoyan | G01B 15/02 |
| | | | 324/635 |
| 2009/0275814 A1 | 11/2009 | Watanabe et al. | |
| 2011/0168575 A1 | 7/2011 | Lica et al. | |
| 2013/0207670 A1* | 8/2013 | Jones | H03B 5/1817 |
| | | | 324/636 |

FOREIGN PATENT DOCUMENTS

| | | |
|---|---|---|
| WO | WO-2011/64770 A2 | 6/2011 |
| WO | WO-2012/007718 A2 | 1/2012 |
| WO | WO-2014/076506 A1 | 5/2014 |
| WO | WO-2014/177707 A1 | 11/2014 |
| WO | WO-2015/015150 A1 | 2/2015 |

OTHER PUBLICATIONS

Stefano Sbrignadello et al: "Electroimpedance Spectroscopy for the Meaurement of the Dielectric Properties of Sodium Chloride Solutions at Different Glucose Concentrations" Journal of Spectroscopy, vol. 24, No. 4-6, Jan. 1, 2013, pp. 1-6.

Yun Fan et al: "Testing glucose concentration in aqueous solution based on microwave cavity perturbation technique", Biomedical Engineering and Informatics, 2010 3rd International Conference On, IEEE, Piscataway, NJ, USA, Oct. 16, 2010, pp. 1046-1049.

* cited by examiner

MEASUREMENT OF SUGAR IN A SOLUTION

TECHNICAL FIELD

The present invention relates to the measurement of sugar content of a solution, in an industrial context.

BACKGROUND

There are many industrial processes where it would be useful to measure sugar content of a solution, typically an aqueous solution.

One notable field where this is useful is during the manufacture of biofuels. In this case, various processes are used to obtain biofuels from plant matter (bio-mass). Plant matter contains cellulose and hemicellulose as the major polysaccharides. Upon hydrolysis, these polysaccharides are converted to glucose and xylose respectively, and both of these sugars can be converted to ethanol. In addition, certain types of plant matter (sugar cane, sugar beet etc.) contain more complex sugars such as sucrose and fructose which can also be converted to ethanol. The produced ethanol can then be mixed with petrol to form the bio-fuel gasohol. During chemical processes such as these, it is advantageous to be able to monitor the sugar content of the processed solutions.

In many applications, although not all, there is a need to measure the amount of sugar continuously in a flowing sample of the a solution, for example as it flows through a pipe. This is typically the case for processes having high throughput. The manufacture of biofuels is an example of where measurement of a flowing sample is needed.

In general in such applications, the ion concentration of the solution can fluctuate unpredictably. The solution may also contain solid material and/or gas bubbles. This can affect various types of measurement, so it is desirable to develop techniques in which the impact of dissolved ions and/or solid material and/or gas bubbles is reduced or removed.

Various techniques for measuring the sugar content of an aqueous solution have been attempted, for example as follows.

Density measurements of an aqueous solution made using, for example, a vibrating tube density meter can determine the sugar concentration if the solution contains predominantly sugar and has a low ion concentration. However, as the ion concentration increases, and/or additionally contains solid material or gas bubbles, a density measurement is liable to give the wrong sugar concentration.

Optical measurements that detect the characteristic absorption bands of the sugar molecules can also be used to determine the sugar concentration. But such techniques require optical access to the solution and the results may be adversely affected by any solid material that reduced optical transmission. The presence of particulate and bubbles can cause dispersion of light, attenuating signal and introducing noise. In practice, this will limit the size of the sample cell and the cross section that may be analyzed. Optical measurement is less reliable since it is prone to coating of windows. In addition, different sugar molecules will produce different optical absorption spectra and so the analysis may be difficult if a mixture of sugars is present in the solution.

Electrical measurements can be made through the wall of a pipe if it is non-metallic. Such electrical measurements will be relatively unaffected by the presence of any gas bubbles and solid material. The measurements can be very fast, allowing for data processing to average signals and remove transient effects caused by the passage of bubble and solid material through the sensing region. However, the electrical permittivity of the solution will generally change as both the sugar content and the water salinity vary. So it is not evident that electrical measurements permit the sugar concentration to be unambiguously determined.

More complex measurements may be taken using techniques such as Fourier Transform Infrared (FT-IR), ultraviolet detection (UV), liquid chromatography (LC), ion chromatography (IC) and LC-mass spectrometry (LC-MS). However, such complex techniques rely on expensive, complex instrumentation. These systems are generally not suitable for inline process monitoring due to their size and requirement for sampling front-ends which require filtration and are prone to clogging. Chromatography and other analytical instrumentation generally have a reasonable response time while the instrument samples, separates and analyze the sample. Chromatography typically takes minutes to separate complex chemical matrices, and FT-IR requires post-processing in software as well as searching and comparison with spectral libraries.

There is a very extensive literature describing the measurement of the glucose concentration in various body fluids, particularly blood, for medical purposes. This is of great importance in the control of diabetes, or monitoring the administration of sugar in water to patients or animals by infusion, for example. However, such techniques are generally applied to small samples that have a relatively low concentration of glucose, for example a few g/L. In an industrial context, it is desirable to use a technique that permits measurement of much higher sugar concentrations.

SUMMARY

According to a first aspect of the present invention, there is provided a method of measuring the amount of sugar in a sample comprising a solution of the sugar, the method comprising:

generating a resonant oscillating electromagnetic field having a first frequency of 100 MHz or more in a cavity resonator containing the sample;

generating a further oscillating electromagnetic field having a second frequency of 100 MHz or less in the sample by driving oscillations in a tank circuit comprising reactive elements that include a reactive probe arranged to generate the further oscillating electromagnetic field in the sample, the first and second frequencies being different frequencies at which the electromagnetic properties of the solution differ;

detecting a characteristic of the resonant oscillating electromagnetic field that is dependent on the electromagnetic properties of the solution;

detecting an electrical parameter of the oscillations of the tank circuit that is a characteristic of the further oscillating electromagnetic field that is dependent on the electromagnetic properties of the solution; and deriving a measure of the amount of sugar from said detected characteristics.

In accordance with this method, there are used oscillating electromagnetic fields at two (or more) different frequencies at which the electromagnetic properties of the solution differ.

A characteristic of the resonant oscillating electromagnetic field at a first frequency of 100 MHz or more is detected using a resonant oscillating electromagnetic field in a cavity resonator containing the sample. A characteristic such as the frequency or amplitude (e.g. characteristics such as loss, q-factor or impedance) of the resonance of the resonant oscillating electromagnetic field may be used. Such characteristics may be representative of the real and imaginary parts of the solution permittivity.

A characteristic of the further oscillating electromagnetic field at a second frequency of 100 MHz or less is detected by driving oscillations in a tank circuit comprising reactive elements that include a reactive probe arranged to generate the oscillating electromagnetic field in the sample. The oscillations may be driven, for example, by a marginal oscillator. An electrical parameter of the oscillations of the tank circuit, such as the oscillation frequency or amplitude, may be detected as the characteristic of the oscillating electromagnetic field.

The differing electromagnetic properties cause different dependence of the detected characteristics on the sugar concentration and other constituents such as ion concentration, the presence of solid material or particulate and/or gas bubbles. This allows the derivation of a measure of the amount of sugar in which the impact of those other constituents is reduced or removed to give a more reproducible, accurate and precise measure of the amount of sugar. As the first frequency is relatively high, the detected characteristic of the resonant oscillating electromagnetic field has a relatively high dependence on the sugar concentration, albeit also affected by the ion concentration of the sample and/or solid material and/or gas bubbles. As the second frequency differs from the first frequency, the detected characteristic of the further oscillating electromagnetic field has a different dependence on the sugar concentration and the other constituents such as the ion concentration and/or solid material and/or gas bubbles, allowing compensation for those other constituents in the derivation of a measure of the amount of sugar.

In addition, the method allows measurements to be taken continuously on a flowing fluid sample, for example a sample flowing through a pipe, because the sensor relies on oscillating electromagnetic fields that may be externally applied, for example through non-conductive walls, without obstructing the fluid flow. In this fashion a reliable, non-invasive, contactless sugar measurement system may be constructed and used for inline analyses of a process stream.

In principle, the method may be applied to any two frequencies, which may be radio frequencies, at which the electromagnetic properties of the solution differ, but more accurate compensation for the other constituents may be achieved by the two frequencies differing by a relatively large amount, for example by at least one order of magnitude, preferably at least two orders of magnitude.

BRIEF DESCRIPTION OF THE DRAWINGS

According to a second aspect of the present invention, there is provided a sensor system that implements a similar method.

Embodiments of the present invention will now be described by way of non-limitative example with reference to the accompanying drawings, in which.

DETAILED DESCRIPTION

Herein, EM refers to "electromagnetic" and RF refers to "radio frequency". As used herein, a radio frequency may in general be considered to be a frequency within the range from 1 kHz to 100 GHz.

Figure 1:
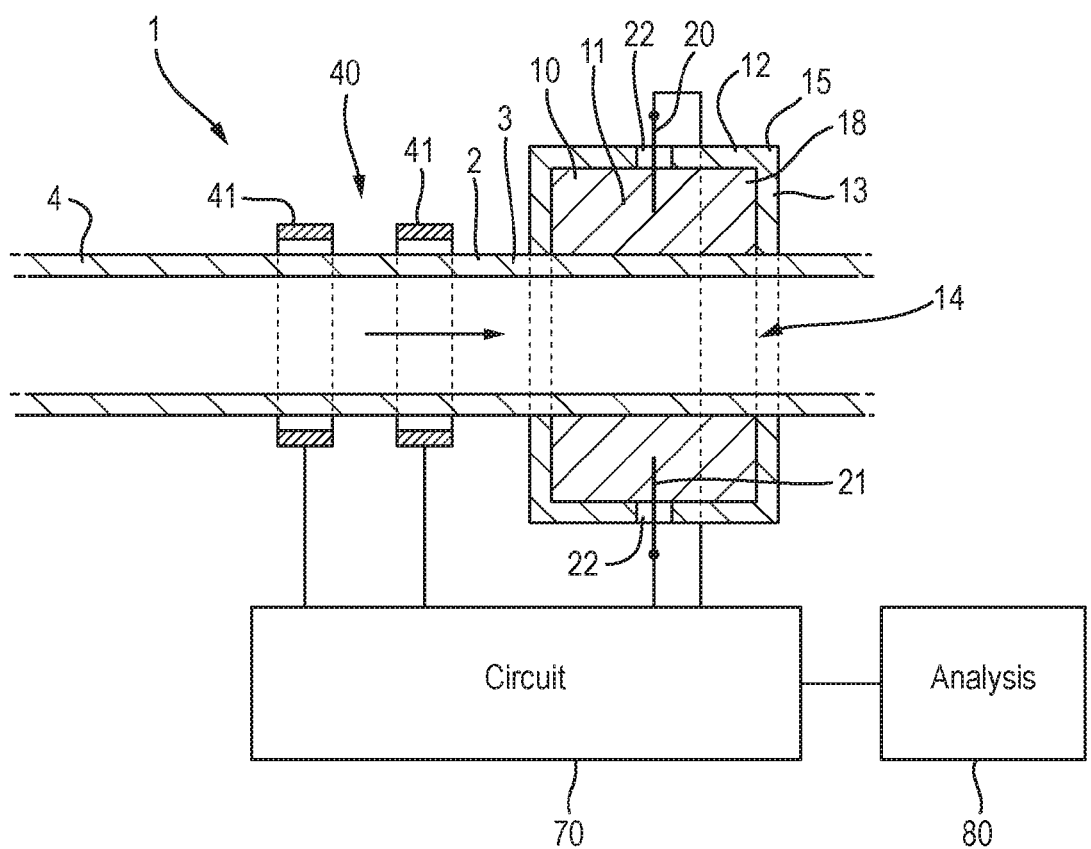
FIG. 1 is a schematic diagram of a sensor system.

FIG. 1 illustrate a sensor system 1 that provides the capability of continuously measuring the sugar concentration in a flowing sample of a solution of the sugar that compensates for a variable ion concentration, and/or a variable content of particulate, solid material and/or gas bubbles.

The sensor system 1 comprises a sample holder 2. The sample holder 2 is formed by tubular walls 3 and forms part of a pipe 4 through which the sample flows. Whilst this arrangement is set up for a flowing fluid sample, the sensor system 1 could equally be applied to a static sample simply by replacing sample holder 2 by a container holding the sample.

The walls 3 of the sample holder 2 are made from a non-conductive material so that it does not interfere with applied EM fields. The walls 3 of the sample holder 2 may be made from an electrically insulating material such as a ceramic, polymer or suitable composite material. The sample holder 2 may have any suitable dimensions commensurate with the formation of applied RF EM fields.

The sample disposed in the sample holder 2 during use comprises a solution in which sugar is dissolved.

In general, the sensor system 1 may be applied to a sample in any industrial process, but the sensor system 1 has particular application in the manufacture of biofuels from organic matter (bio-mass) such as sugar cane. In that case, the sample could be a solution that is processed as part of the manufacture, for example as discussed above in the introduction to this specification. During such chemical processes, it is desired to monitor the sugar content of the processed solutions.

The sugar may be a monosaccharide, a disaccharide, or an oligosaccharide. A monosaccharide or a disaccharide is preferred. In the case of an oligosaccharide, then the sugar may typically contain 3 to 9 saccharide units, preferably 3 to 6 saccharide units, for example three or four saccharide units.

Some non-limitative examples of the types of sugar are: glucose, mannose, galactose, fructose, ribose, deoxyribose, xylose, sucrose, maltose or lactose. The sugar may comprise plural different types of sugar, including the above examples and/or others in any combination.

The solution is typically an aqueous solution.

The sugar is soluble in the solution. By way of example, the sugar may have a degree of solubility such that at least 1 g of the sugar dissolves in 1 L of water at room temperature.

The solution may contain other components, for example other solutes, acids, salts, other ions such as metallic ions, and solid material, such as suspended particles, carbonates, and/or bubbles of gas, such as air.

The sensor system 1 may be used to measure samples with a concentration of sugar from trace levels (e.g. parts per million by volume) extending up to relatively high levels, for example of the order of hundreds of g/L. The sensor system 1 may be applied to samples having a concentration of sugar greater than 15 g/L, more often greater than 25 g/L.

The sensor system 1 generates oscillating EM fields in the sample holder 2 at two radio frequencies at which the EM properties of the solution differ.

As shown in FIG. 1, the sensor system 1 includes, disposed around the sample holder 2: a cavity resonator 10 having a transmission antenna 21 and a reception antenna 22; and a probe 40 comprising a pair of conductive rings 41. The transmission antenna 20, the reception antenna 21 and the pair of conductive rings 41 are all connected to an electrical circuit 70. The cavity resonator 10 forms part of a high frequency module that generates the oscillating EM field of higher frequency, whereas the probe 40 forms part of a low frequency module that generates the oscillating EM field of lower frequency.

The cavity resonator 10 forms part of a measurement apparatus of the high frequency module and will now be described.

The cavity resonator 10 comprises a casing 15 defining a cavity 11. The casing 15 is electrically conductive, typically being made of metal. The casing 15 is generally cylindrical, comprising a cylindrical wall 12 and end walls 13 that close the ends of the cylindrical wall 12. The end walls 13 have a pair of opposed openings 14 that are aligned along the cylindrical axis of the cylindrical wall 12 and through which the sample holder 2 extends, so that the cavity resonator 10 contains the sample.

In the example shown in FIG. 1, the casing 15 is formed as a continuous piece entirely enclosing the cavity 11 except for the openings 14. However, the casing 15 could alternatively be made from multiple pieces and/or have apertures that are sufficiently small relative to the EM wavelength to prevent leakage of the EM field.

The cavity resonator 10 further comprises insulator material 18 disposed inside the cavity 11 between the casing 15 and the sample holder 2. The insulator material 18 may in general be a solid, liquid or gas, but a solid is most convenient.

The transmission antenna 20 and the reception antenna 21 are disposed within the cavity 11, positioned on opposite sides thereof. Each of the antennae 20 and 21 is mounted in the cylindrical wall 12 in respective connectors 22 that electrically insulate the antennae 20 and 21 from the cylindrical wall 12. In use, the casing 15 is grounded, and there is a potential difference between the casing 15 and the antennae 20 and 21.

The transmission antenna 20 is used to generate a resonant oscillating EM field inside the cavity 11. The reception antenna 21 is used to detect that resonant EM field. The wavelength of the EM radiation exceeds the cut-off wavelength of the openings 14 so that the EM radiation is unable to escape therethrough. The resonant EM field has modes defined by the configuration of the cavity 11, typically having the greatest field strength in the center of the cavity 11. Thus, the resonant EM field interacts with the sample in the sample holder 2.

Figure 2:
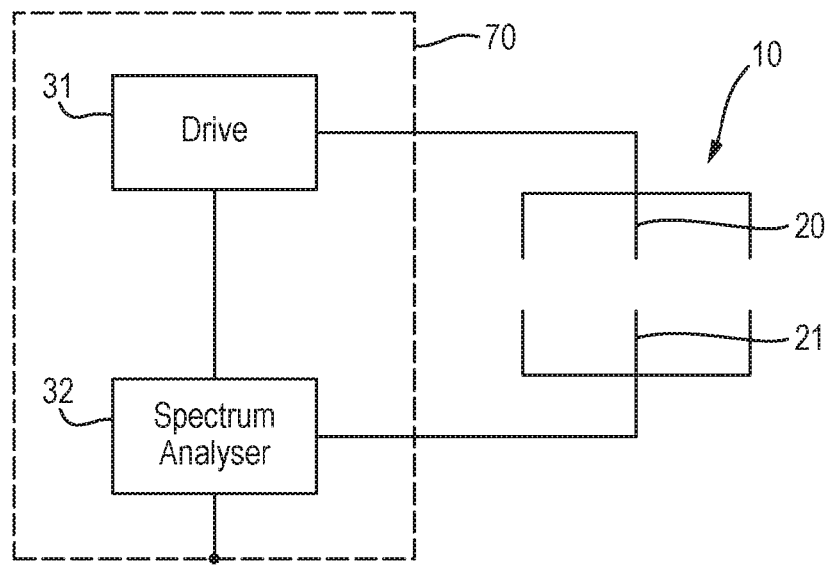
FIG. 2 is a circuit diagram of a high frequency module of the sensor system employing a cavity resonator.

The cavity resonator 10 is connected to components of the electrical circuit 70 shown in FIG. 2 that form the remainder of the high frequency module and are arranged as follows.

The electrical circuit 70 comprises a drive circuit 31 connected to the transmission antenna 20 to form part of the measurement apparatus of the high frequency module. The drive circuit 31 is arranged to drive the transmission antenna 20 to generate a resonant EM field inside the cavity 11. The drive circuit 31 may generate a resonant EM field that can be varied across a range of frequencies. The cavity resonator 10 is designed to support modes in such frequencies, typically to support a single mode such as the TE111 mode.

The electrical circuit 70 further comprises a spectrum analyzer 32 connected to the reception antenna 21. The spectrum analyzer 32 forms the detection system of the high frequency module and is arranged to derive a measure of at least one characteristic of the resonant EM field in the cavity 11. The spectrum analyzer 32 measures the response across a range of frequencies and derives the characteristic therefrom, in a conventional manner. Thus, the spectrum analyzer 32 is connected to the drive circuit 31 to obtain information about the drive frequency at any given time.

The characteristic, or each characteristic where there are plural, is one that is dependent on the EM properties of the contents of the cavity 11 and therefore of the sample in the sample holder 2. The complex electrical permittivity of the sample can be determined by measuring such characteristics of a cavity resonator. For example the resonance frequency and amplitude of the resonance may provide a measure of the real and imaginary parts of the permittivity of the solution respectively.

One characteristic that may be selected is the resonance frequency, i.e. the frequency at which the amplitude of the response is maximum. The resonance frequency is not substantially affected by losses in the cavity 11. If the cavity 11 is modeled as a parallel resistance R, inductance L and capacitance C, then the resonance frequency $\omega 0 = 1/\sqrt{(LC)}$ which is not dependent on R which represents the losses in the cavity.

Other characteristics that may be selected include parameters that are dependent on the losses inside the cavity. Suitable parameters, and their RLC representation if the cavity is modeled as a parallel resistance R, inductance L and capacitance C are: the resonance bandwidth $\Delta\omega = 1/(RC)$; or the Q-factor $Q = R\sqrt{(C/L)}$, which are both dependent on R which represents the losses in the cavity. The resonance bandwidth is the 3 dB bandwidth.

Characteristics may similarly be derived from the phase response.

Although in this example, a single cavity resonator 10 is employed, alternatively the cavity resonator 10 may be replaced by a cavity resonator system that comprises a primary resonator and a secondary resonator arranged as described in WO-2014/076506 to provide compensation for exterior effects. In that case, the electrical circuit 70 is also correspondingly modified as described in WO-2014/076506.

The oscillating EM field of higher frequency typically has a frequency of at least 100 MHz. The operating frequency is determined by the dimensions of the cavity 11 of the cavity resonator 10, and these dimensions are dependent on the dimensions of the sample holder 2. The frequency is typically chosen to be close to 1 GHz since the size of resonant cavities with this resonance frequency is well matched to typical pipes with diameters of several centimeters.

For practical reasons, the oscillating EM field of higher frequency may have a frequency of at most 10 GHz. In that range, it is possible to make measurements without inserting the antennae 20 and 21 through the walls 3 of the sample holder 2 where they may obstruct the flow of the sample. It is possible to operate above 10 GHz but the sensor system 1 becomes more difficult to configure and there is a risk of the antenna 20 and 21 becoming damaged by the sample and/or blocking the flow, particularly if the sample contains solid debris etc.

The probe 40 forms part of a measurement apparatus of the low frequency module and will now be described.

The conductive rings 41 form electrodes that capacitively couple through the walls 3 of the sample holder 2 with the sample inside, and hence with each other by virtue of the fluid coupling properties. Accordingly, the probe 40 is a capacitive probe that forms the sensing region between the conductive rings 41 so that the sensing region extends across the interior of the sample holder 2. This form of the probe 40 allows the contents of the sample holder 2 to be sensed with a construction that is straightforward to implement without physically disrupting flow of the sample. The geometry of the conductive rings 41, the sample holder 2 and the frequency of operation can be adjusted to provide the best sensitivity over the desired range of the characteristic being sensed.

Many other forms of the probe 40 could be used to provide a capacitive probe. In the case of sensing the contents of a pipe, the probe 40 could take other forms such as plates extending only partway around the pipe, although the capacitive rings 41 have the advantage of providing an extensive sensing region with a simple construction. When used to sense other systems, the probe 40 could have an entirely different construction, ranging for example from a simple pair of planar plates to more complicated structures (e.g. planar or digital arrays across which samples may flow).

As an alternative, the probe 40 could be an inductive probe such as a cylindrical coil wrapped around the pipe that forms a sensing region that extends from inside the coil to a region around the ends of the coil. Likewise, the probe 40 could be provided as a center rod inside a coaxial ring or cylinder. More generally, the probe could be any form of reactive probe.

Figure 3:
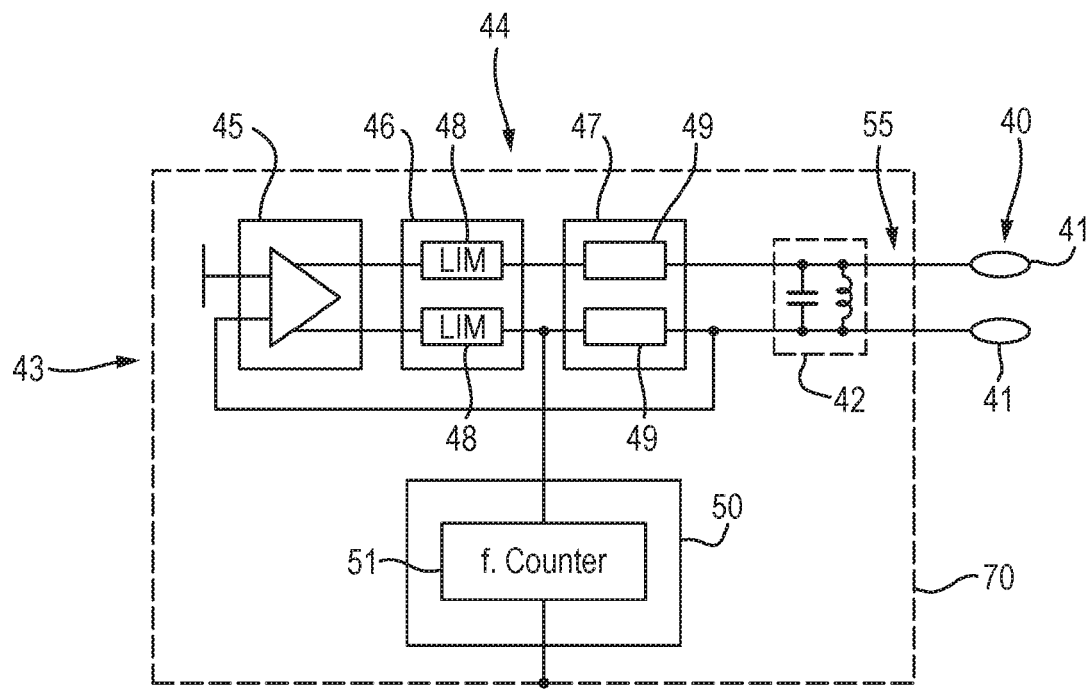
FIG. 3 is a circuit diagram of a low frequency module of the sensor system employing an oscillator.

The pair of conductive rings 41 of the probe 40 are connected to components of the electrical circuit 70 shown in FIG. 3 that form the remainder of the low frequency module and are arranged as follows.

The electrical circuit 70 comprises the following components connected to the probe 40 to form part of the measurement apparatus of the low frequency module.

The electrical circuit 70 comprises further reactive elements 42 connected in parallel to the probe 40, so that the probe 40 and further reactive elements 42 together form a tank circuit 55. In FIG. 3, the reactive elements 42 are illustrated schematically as an inductor and a capacitor in parallel, but in general the tank circuit 55 could include any arrangement of reactive elements, one of which is the probe 40.

The electrical circuit 70 comprises an oscillator circuit 43 arranged in this example as a marginal oscillator, as follows. The oscillator circuit 43 is arranged to drive oscillations in the tank circuit 55.

The oscillator circuit 43 includes a non-linear drive circuit 44 that provides differential signaling in that it supplies a differential signal pair of complementary signals across the tank circuit 55. The complementary signals are each formed with respect to a common ground, but in anti-phase with each other, although they may have unbalanced amplitudes as described further below. Thus, the overall signal appearing across the tank circuit 55 is the difference between the complementary signals and is independent of the ground, which provides various advantages to the sensor system 1.

The non-linear drive circuit 44 has the following arrangement that sustains the oscillation on the basis of one of the complementary signals supplied back to the non-linear drive circuit 44. In this example, the oscillator circuit 43 is a Robinson marginal oscillator including a separate gain stage 45 and limiter stage 46, the limiter stage 46 driving a current source stage 47. Although use of a Robinson marginal oscillator is not essential, this provides the advantages of a Robinson marginal oscillator that are known in themselves.

The gain stage 45 is supplied with a single one of the complementary signals fed back from the tank circuit 55 and amplifies that signal to provide a differential pair of amplified outputs. The gain stage 45 is formed in this example by an operational amplifier that amplifies the complementary signal supplied back from the tank circuit 55. That complementary signal from the tank circuit 55 is DC coupled to one of the inputs of the operational amplifier, the other input of the operational amplifier being grounded.

The limiter stage 46 is supplied with the differential pair of amplified outputs from the gain stage 45 and limits those outputs to provide a differential pair of limited outputs. In this example, the limiter stage 46 is formed by a pair of limiters 48 that each limit the amplitude of one of the differential pair of amplified outputs.

The current source stage 47 is driven by the differential pair of limited outputs from the limiter stage 46 and converts them into the differential signal pair of complementary signals that are supplied across the tank circuit 55. The current source stage 47 converts the voltage signals into currents and has a differential output. The current source stage 47 comprises a pair of current sources 49 each receiving one of the limited outputs. Each current source 49 may be formed by a passive element, for example a resistor or a capacitor that converts the voltage of the input into a current. Alternatively, each current source 49 may be an active component such as a semiconductor device or an amplifier. The feedback of the complementary signal from the tank circuit 55 to the gain stage 45 is positive and in combination with the action of the limiter stage 46 builds up and sustains the oscillation of the tank circuit 55 at the natural frequency of the tank circuit 55.

The current sources 49 may be identical so that the complementary signals supplied across the tank circuit 55 are of equal amplitude. However, advantageously the current sources 49 may be unbalanced, that is have different voltage-to-current gains. As a result, the complementary signals supplied across the tank circuit 55 have unbalanced amplitudes. By creating such a difference in the amplitudes of the complementary signals to ensure that the inverting output is more dominant than the non-inverting output, reliable starting of the oscillator circuit 43 is achieved. The unbalanced nature of the complementary signals provides an anti-hysteresis effect.

The oscillator circuit 43 may have the construction disclosed in greater detail in PCT/GB2014/051886 which is incorporated herein by reference.

The electrical circuit 70 also includes a detection circuit 50 that forms the detection system of the low frequency module. The detection circuit 50 is arranged to detect an electrical parameter of the oscillations of the tank circuit 55 which is therefore a characteristic of the oscillating EM field generated by the probe 40. The characteristic, or each characteristic where there are plural, is one that is dependent on the EM properties of the sample in the sample holder 2. The complex electrical permittivity of the sample can be determined by measuring such electrical parameters of the oscillations. For example, the oscillation frequency and amplitude may provide a measure of the real and imaginary parts of the permittivity of the solution.

One characteristic that may be selected is the frequency of the oscillations. In that case, the detection circuit may comprise a frequency counter 51 as shown in FIG. 3. Such a frequency counter 51 may be implemented in a microcontroller. The frequency counter 51 is supplied with one of the outputs of the limiter stage 46 (although in general it could be supplied with an oscillating signal from any other point in the oscillator circuit 43). The frequency counter 51 serves as a detector that detects the frequency of the oscillation of the tank circuit 55 and outputs a signal representing that frequency of oscillation. The EM properties of sample on which this type of characteristic is dependent are the real part of the electric or magnetic permittivity.

Another characteristic that may be selected is the amplitude of the oscillation of the tank circuit 55. The EM properties of the contents of the sensing region on which this type of characteristic is dependent are the imaginary part of the electric or magnetic susceptibility, that is the losses or conductivity. In this case, the amplitude of the oscillation of the tank circuit 55 may be detected differentially. This is not essential, but further improves the stability and sensitivity, and reduces the impact of thermal drift, for example.

In general, any other characteristic of the oscillation could be additionally or alternatively detected, for example the Q factor.

The oscillating EM field of lower frequency is chosen so that the two radio frequencies are sufficiently different to provide accurate compensation as discussed further below, for example differing by at least one order of magnitude, preferably at least two orders of magnitude.

The oscillating EM field of lower frequency typically has a frequency of at most 100 MHz. That frequency can be tuned by altering the values of the components in the oscillator circuit 43, but typically values greater than 100 MHz are difficult to implement. The frequency is typically chosen to be close to 10 MHz, because that allows the RF signal to be capacitively coupled efficiently into the sample through the walls 3 of the sample holder 2. If the dimensions of the sample holder 2 are changed, the values of the components can be changed to bring the frequency back close to 10 MHz.

For practical reasons, the oscillating EM field of lower frequency may have a frequency of at least 1 MHz. It is more difficult to make measurements below 1 MHz due to the weaker capacitive coupling of the RF signals through the walls 3 of the sample holder 2 into the sample.

A particular benefit of the use of EM fields is that the measurements may be taken continuously on the sample as it flows through the sample holder 2. Thus, the sensor system 1 is effective at relatively high flow rates.

Signals representing the characteristics of the oscillating EM fields are fed from the electrical circuit 70, in particular from the spectrum analyzer 32 and the detection circuit 50, to an analysis system 80 for subsequent analysis. The analysis system 80 may be any form of circuit that is capable of performing the analysis, for example a dedicated hardware or a microprocessor running an appropriate program.

The analysis system 80 derives a measure of the amount of sugar in the sample from the characteristics detected at the two radio frequencies, as follows. The measure is derived continuously as the sample flows through the sample holder 2. In the following, the measure of the amount of sugar is referred to as the sugar concentration, but in general it may be any measure of the amount.

These measurements are affected to a different extent by changes in the sugar concentration and other constituents such as ion concentration, solid particles and/or gas bubbles. By combining the values of these measurements at different radio frequencies, the effects of changes in the other constituents can then be removed to give an unambiguous value for the sugar concentration. For example, the analysis system 80 may combine the characteristics detected at said at least two radio frequencies to cancel the effect of conductive ions and/or gasses and/or solids in the solution.

The use of low frequency and high frequency measurements to determine the complex electrical permittivity of aqueous solutions with variable salinity is well documented. The real part of the permittivity describes the ability of the solution to store electrical energy, which affects its capacitance. The imaginary part of the permittivity describes the ability of the solution to adsorb or dissipate electrical energy as heat or loss, which affects electrical resistance.

In the high frequency module, the real and imaginary parts of the permittivity may be determined via their effect on the resonance peak frequency, or other characteristics such as amplitude, in the cavity resonator 10. In the low frequency module, the real and imaginary parts of the permittivity may be determined via their effect on the oscillation frequency, or other characteristics such as amplitude, in the oscillator circuit 43.

The presence of sugar molecules in an aqueous solution reduces the extent of the hydrogen bonding between water molecules, and reduces the value of the real part of the water permittivity. In the cavity resonator 10, the frequency of the resonance peak will shift to a higher frequency. In the oscillator circuit 43, the capacitance of the circuit will reduce and the oscillation frequency increase.

The presence of salt ions also reduces the extent of the hydrogen bonding between the water molecules, reducing both the circuit oscillation frequency and resonance peak frequency. However, the influence of the electrically-charged salt ions on the electrical properties is more complex, and varies much more strongly with the value of the radio frequency. Their influence is strong at low frequencies, but weakens as the radio frequency increases, for example becoming very small for frequencies above 100 GHz.

At lower frequencies, the salt ions are able to move in response to the changing electric field and the electrical conductivity of the solution increases as the salt content increases. The effect of the changing electrical properties of the solution on the low frequency oscillator circuit will then depend upon the form of the circuit and the values of the electrical components. The capacitance and electrical resistance of the portion of fluid between the electrodes will vary with water salinity and sugar content, causing the oscillator frequency and amplitude to change in a complicated, but reproducible, manner.

Figure 4:
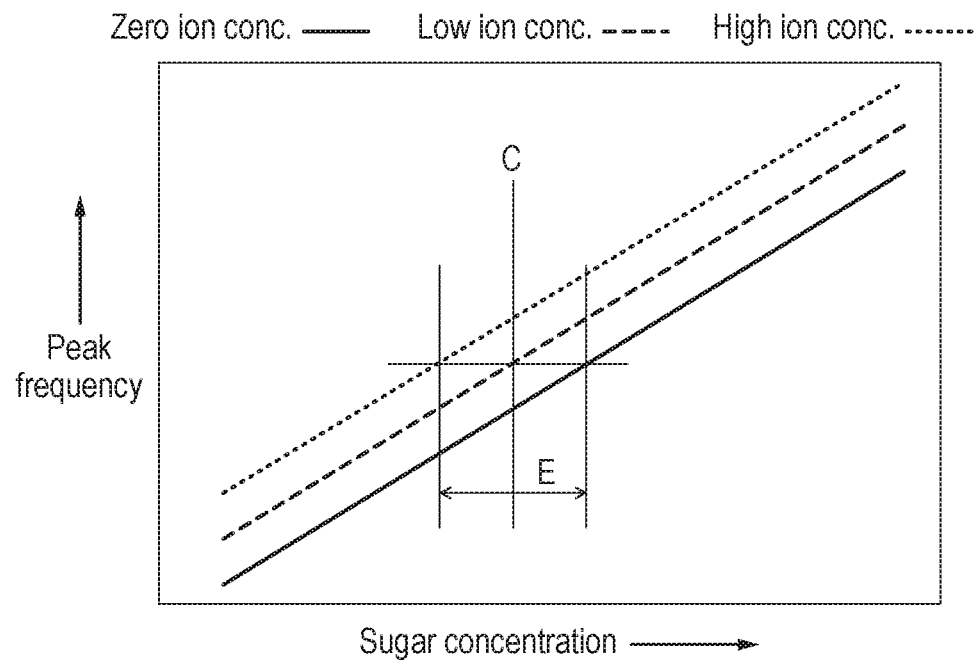
FIG. 4 is an illustrative graph for the high frequency module, plotting the detected resonance frequency against sugar concentration for different ion concentrations.

The peak frequency in the high frequency resonator is mainly determined by the sugar in the solution, but variations in the water salinity would cause a considerable error in a measure of sugar concentration derived from that high frequency measurements alone. This is illustrated in FIG. 4 which shows the high frequency response with sugar concentration for three different ion concentrations that might typically be encountered (zero, low and high ion concentrations). As can be seen, the resonance frequency provides a reasonable accurate measure of the average sugar concentration C, but with an error E due to the change in ion concentration.

Figure 5:
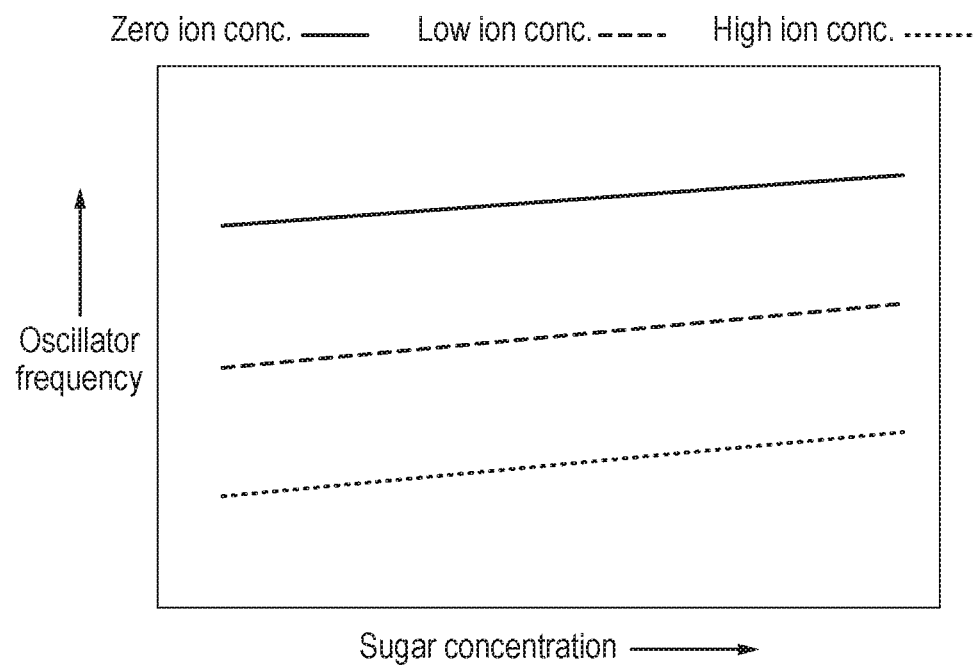
FIG. 5 is an illustrative graph for the low frequency module, plotting the detected oscillation frequency against sugar concentration for different ion concentrations.

In contrast, the oscillation frequency in the low frequency circuit is mainly determined by the water salinity because of the stronger effect of the salt ions on the electrical properties at lower frequencies. The precise form of the variation with salinity will depend upon the details of the oscillator circuit 43. However, FIG. 5 shows a representative low frequency response with sugar concentration for the same three different ion concentrations as FIG. 4. As can be seen, the frequency of the oscillations is weakly dependent on the sugar concentration, but strongly dependent on the sugar concentration.

By algebraically combining the characteristics measured at the two radio frequencies, a measure of sugar concentration can be calculated that varies with the sugar content but which is independent of the ion concentration.

The combination may be performed as follows in the case that the resonance frequency fpeak and the oscillation frequency fosc vary linearly with both the sugar concentration [sugar] and the salt concentration [salt]. In this case the dependence may be represented by the following equations:

$$f_{peak} = f_{peak0} + a \cdot [\text{sugar}] + b \cdot [\text{salt}]$$

$$f_{osc} = f_{osc0} + c \cdot [\text{sugar}] - d \cdot [\text{salt}]$$

where $f_{peak0}$ and $f_{osc0}$ are, respectively, the resonance frequency and oscillator frequency values when the solution contains no sugar or ions, and a, b, c, and d are constant values determined by calibration. The measure of sugar concentration may be derived as a "corrected" resonance frequency according to the equation:

$$f_{peakcorr} = f_{peak} + (b/d) \cdot f_{osc}$$

Expanding that equation provides:

$$f_{peakcorr} = f_{peak0} + (b/d) \cdot f_{osc0} + (a + (b \cdot c)/d) \cdot [\text{sugar}] + (b-b) \cdot [\text{salt}]$$

Thus, the dependence on the ion concentration vanishes, showing that the measure of sugar concentration fpeakcorr is dependent on only the sugar concentration.

Measurements show that both fpeak and fosc typically both vary linearly with the sugar content. It is observed that fpeak and fosc vary in a more complicated manner with the ion concentration, but the response can be made linear over the typical ranges of ion concentrations experienced in practical applications by adjustment of the component values in the oscillator circuit 43. Alternatively, the analysis above can be adapted to take account of any non-linear variation observed in practice.

To validate the operation of the sensor system 1, measurements have been made on solutions containing glucose and/or xylose with a total sugar concentration in the range 0 g/L up to 175 g/L. These measurements show that the electrical properties of the solution depend only on the total concentration of sugar (mass per volume) regardless of its form, so the concentrations of glucose and xylose are not separately determined.

Figure 6:
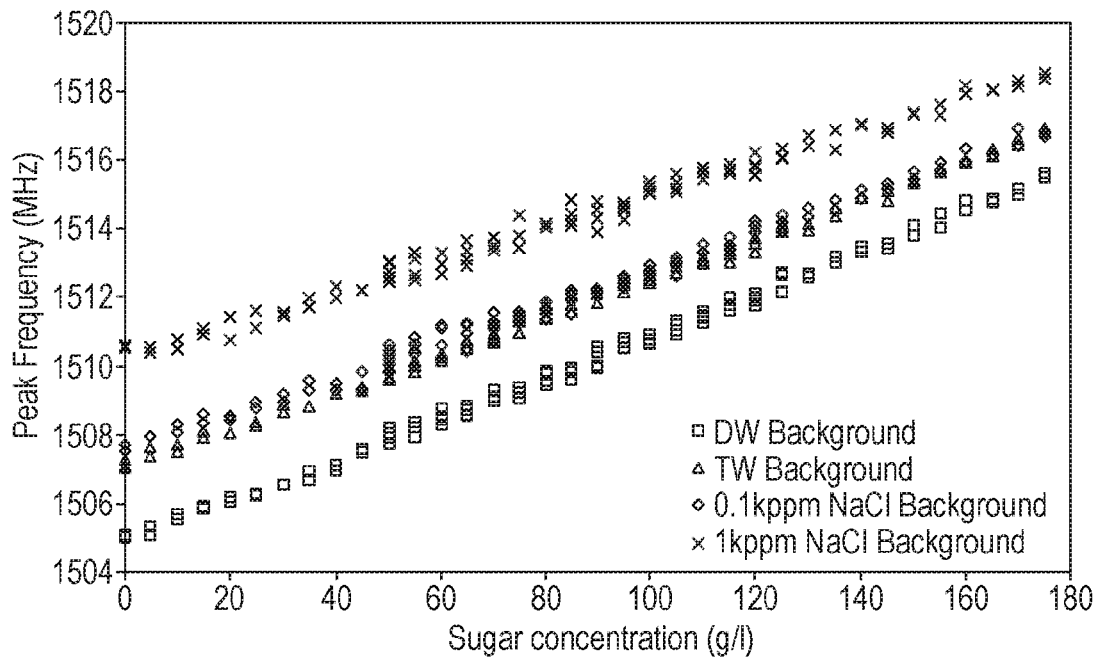
FIG. 6 is a graph of experimental results from the high frequency module, plotting the detected resonance frequency against sugar concentration for different ion concentrations.
Figure 7:
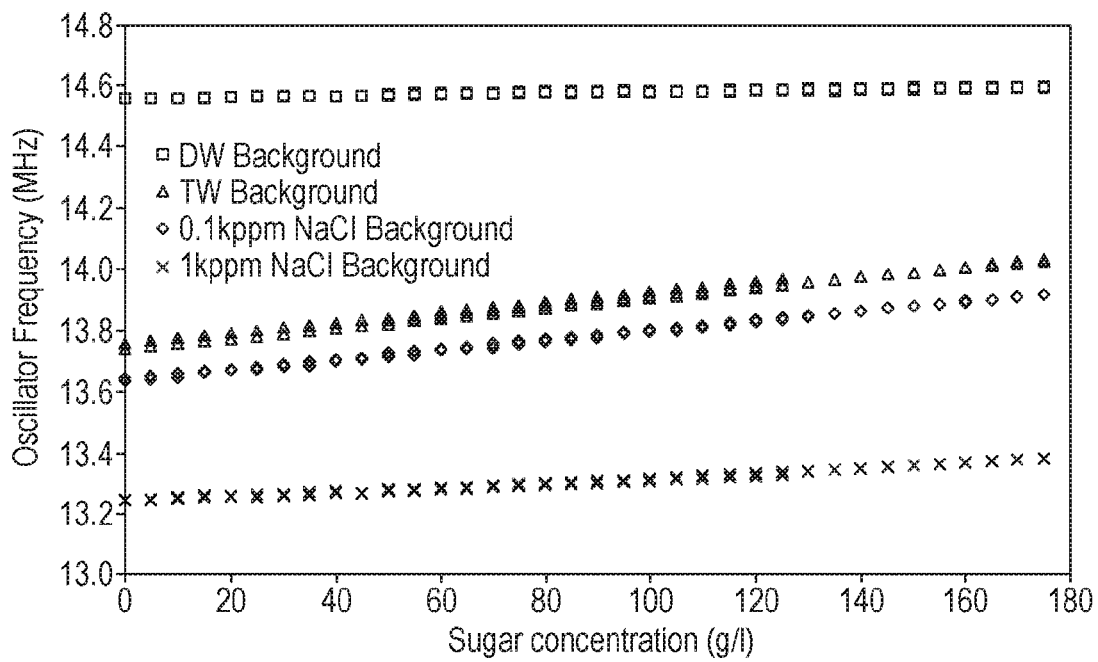
FIG. 7 is a graph of experimental results from the low frequency module, plotting the detected frequency against sugar concentration for different ion concentrations.

FIGS. 6 and 7 below show the electrical properties of solutions with different sugar concentrations and different ion concentrations.

FIG. 6 shows the variation of the resonance frequency of the high frequency module for solutions in which the sugar concentration varies between 0 g/L and 175 g/L using four different water salinities (ion concentrations), in particular distilled water, tap water, 0.1 kppm NaCl and 1 kppm NaCl.

The value of the peak frequency is strongly dependent on the sugar concentration, but weakly affected by the water salinity.

FIG. 7 shows the variation of the oscillation frequency of the low frequency module for the same set of solutions. The value of the oscillation frequency is mainly determined by the water salinity, with a smaller dependence on the sugar concentration.

The oscillator frequency data fosc may be combined with the peak frequency data fpeak to provide a measure of sugar concentration as composite value fpeakcorr according to the following equation:

$$f_{peakcorr} = f_{peak} + 0.35 f_{osc}$$

Figure 8:
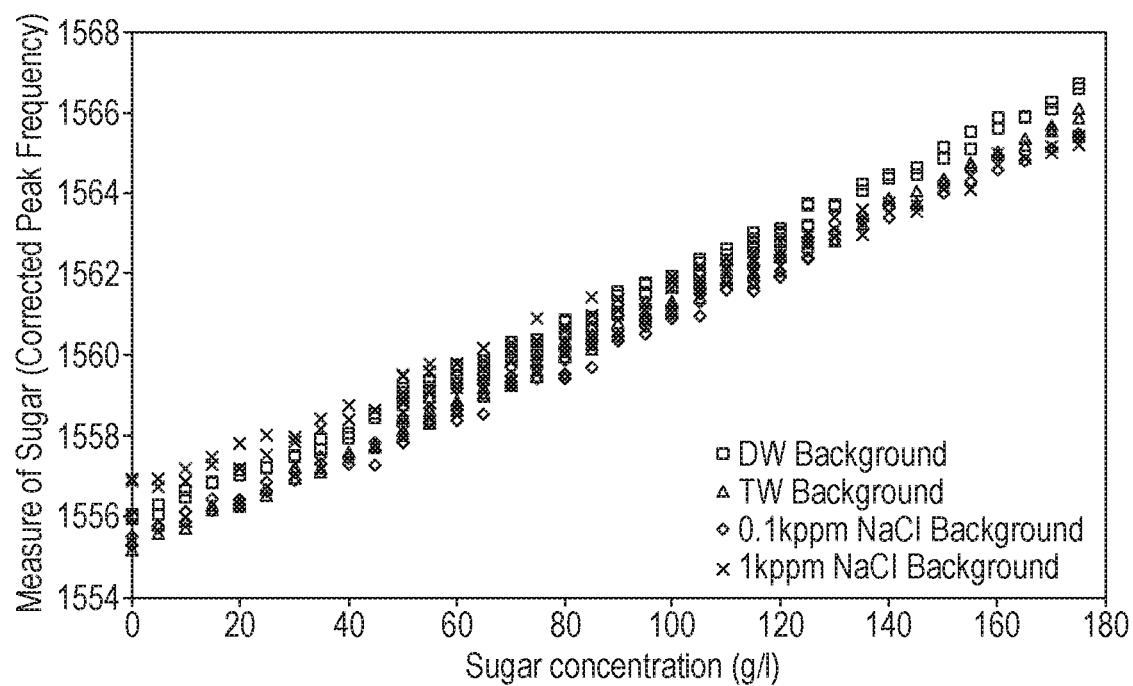
FIG. 8 is a graph of a measure of the amount of sugar derived from the results of FIGS. 6 and 7, plotted as a corrected value of the detected resonance frequency of FIG. 6 against sugar concentration for different ion concentrations.

FIG. 8 shows a plot of fpeakcorr versus sugar content for all of the data at different salinities, giving a straight line. The error is the sugar content caused by changes in the water salinity is now approximately ±10 g/L.

Although the above disclosure is presented with reference to compensating for the effect of the ion concentration, similar effects and considerations apply to other constituents such as solid material and gas bubbles.

The sensor system 1 described above uses two radio frequencies and takes measurements using two different techniques in the high and low frequency modules, i.e. employing a cavity resonator 10 and an oscillator circuit 43 respectively. That is advantageous for the reasons described above, but other approaches using two radio frequencies can alternatively be applied. The high and low frequency modules can use the same measurement technique as each other, for example each employing a cavity resonator 10 or each employing an oscillator circuit 43. Similarly, techniques other than employing a cavity resonator 10 may be applied to the high frequency module and techniques other than employing an oscillator circuit 43 may be applied to the high frequency module. In another alternative, more than two radio frequencies may be used.

The invention claimed is:

1. A method of measuring the amount of sugar in a sample comprising a solution of the sugar, the method comprising:
    generating a resonant oscillating electromagnetic field having a first frequency of 100 MHz or more in a cavity resonator containing the sample;
    generating a further oscillating electromagnetic field having a second frequency of 100 MHz or less in the sample by driving oscillations in a tank circuit comprising reactive elements that include a reactive probe arranged to generate the further oscillating electromagnetic field in the sample, the first and second frequencies being different frequencies at which the electromagnetic properties of the solution differ;
    detecting a characteristic of the resonant oscillating electromagnetic field that is dependent on the electromagnetic properties of the solution;
    detecting an electrical parameter of the oscillations of the tank circuit that is a characteristic of the further oscillating electromagnetic field that is dependent on the electromagnetic properties of the solution; and
    deriving a measure of the amount of sugar from said detected characteristics.

2. A method according to claim 1, wherein said characteristic of the resonant oscillating electromagnetic field is the resonance frequency of the resonant oscillating electromagnetic field.

3. A method according to claim 1, wherein said oscillations in said tank circuit are driven by a marginal oscillator.

4. A method according to claim 3, wherein said electrical parameter of the oscillations of the tank circuit is the frequency of the oscillations.

5. A method according to claim 1, wherein said measure of the amount of sugar from said detected characteristics is derived by combining said detected characteristics to cancel the effect of conductive ions and/or gasses and/or solids in the solution.

6. A method according to claim 1, wherein the two frequencies differ by at least one order of magnitude.

7. A method according to claim 1, wherein the two frequencies differ by at least two orders of magnitude.

8. A method according to claim 1, wherein the sample is a flowing fluid sample.

9. A method according to claim 1, wherein the sample is a sample taken from a process of manufacture of a biofuel.

10. A method according to claim 1, wherein the solution is an aqueous solution.

11. A method according to claim 1, wherein said first and second frequencies are radio frequencies.

12. A sensor system for measuring the amount of sugar in a sample comprising a solution of the sugar, the sensor system comprising:
a measurement apparatus comprising:
a cavity resonator arranged to contain the sample,
a transmission antenna disposed in the cavity resonator,
a drive circuit arranged to drive the transmission antenna to generate a resonant oscillating electromagnetic field having a first frequency of 100 MHz or more in the cavity resonator,
a tank circuit comprising reactive elements that include a reactive probe arranged to generate a further oscillating electromagnetic field in the sample, and
an oscillator circuit arranged to drive oscillations in the tank circuit that cause the probe to generate the further oscillating electromagnetic field having a second frequency of 100 MHz or less, the first and second frequencies being different frequencies at which the electromagnetic properties of the solution differ;
a detection system comprising:
a reception antenna disposed in the cavity resonator,
a resonant cavity detection circuit connected to the reception antenna and arranged to detect a characteristic of the resonant oscillating electromagnetic field that is dependent on the electromagnetic properties of the sample,
a tank circuit detection circuit arranged to detect an electrical parameter of the oscillations of the tank circuit that is a characteristic of the further oscillating electromagnetic field that is dependent on the electromagnetic properties of the solution; and
an analysis system arranged to derive a measure of the amount of sugar from said detected characteristics.

13. A sensor system according to claim 12, wherein said characteristic of the resonant oscillating electromagnetic field is the resonance frequency of the resonant oscillating electromagnetic field.

14. A sensor system according to claim 12, wherein said oscillator circuit is a marginal oscillator.

15. A sensor system according to claim 14, wherein said electrical parameter of the oscillations of the tank circuit is the frequency of the oscillations.

16. A sensor system according to claim 12, wherein the analysis system is arranged to derive said measure of the amount of sugar from said detected characteristics by combining said detected characteristics to cancel the effect of conductive ions and/or gasses and/or solids in the solution.

17. A sensor system according to claim 12, wherein the two frequencies differ by at least one order of magnitude.

18. A sensor system according to claim 12, frequencies differ by at least two orders of magnitude.

19. A sensor system according to claim 12, wherein the sample is a flowing fluid sample.

20. A sensor system according to claim 12, wherein the sample is a sample taken from a process of manufacture of a biofuel.

21. A sensor system according to claim 12, wherein the solution is an aqueous solution.

22. A sensor system according to claim 12, wherein the first and second frequencies are radio frequencies.

23. A sensor system according to claim 12 in combination with said sample.

* * * * *